(12) United States Patent
Teshima et al.

(10) Patent No.: US 7,566,728 B2
(45) Date of Patent: Jul. 28, 2009

(54) REMEDY FOR SLEEP DISTURBANCE (75) Inventors: Koji Teshima, Tokyo (JP); Masanori Minoguchi, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 544 days.

(21) Appl. No.: 10/508,339

(22) PCT Filed: Mar. 28, 2003

(86) PCT No.: PCT/JP03/03925

§ 371 (c)(1),
(2), (4) Date: Oct. 25, 2004

(87) PCT Pub. No.: WO03/082333

PCT Pub. Date: Oct. 9, 2003

(65) Prior Publication Data

US 2005/0119308 A1    Jun. 2, 2005

(30) Foreign Application Priority Data

Mar. 29, 2002    (JP)    ............... 2002-093398

(51) Int. Cl.
*A61K 31/454*    (2006.01)
(52) U.S. Cl. .................. 514/322; 546/199
(58) Field of Classification Search ........ 514/310, 514/322
See application file for complete search history.

(56) References Cited

U.S. PATENT DOCUMENTS

| | | | |
|---|---|---|---|
| 6,043,366 A | 3/2000 | Adam et al. | |
| 6,071,925 A | 6/2000 | Adam et al. | |
| 6,113,527 A * | 9/2000 | Adam et al. | ........... 514/210.07 |
| 6,166,209 A | 12/2000 | Adam et al. | |
| 6,172,067 B1 | 1/2001 | Ito et al. | |
| 6,258,825 B1 | 7/2001 | Ozaki et al. | |
| 6,277,991 B1 | 8/2001 | Hohlweg et al. | |
| 6,340,681 B1 | 1/2002 | Ito | |
| 6,410,561 B1 | 6/2002 | Shinkai et al. | |
| 6,423,725 B1 * | 7/2002 | Ito et al. | ..................... 514/322 |
| 6,465,478 B1 | 10/2002 | Ito et al. | |
| 6,635,653 B2 | 10/2003 | Goehring et al. | |
| 6,642,247 B2 | 11/2003 | Adam et al. | |
| 2001/0041746 A1 | 11/2001 | Kyle et al. | |
| 2002/0035110 A1 | 3/2002 | Bentley et al. | |
| 2002/0049212 A1 | 4/2002 | Ito et al. | |
| 2002/0128288 A1 | 9/2002 | Kyle et al. | |
| 2003/0008886 A1 | 1/2003 | Goehring et al. | |
| 2003/0013874 A1 | 1/2003 | Goehring et al. | |
| 2003/0018041 A1 | 1/2003 | Goehring et al. | |
| 2003/0027834 A1 | 2/2003 | Goehring et al. | |
| 2003/0055087 A1 | 3/2003 | Shinkai et al. | |
| 2003/0078278 A1 | 4/2003 | Ito et al. | |
| 2003/0078279 A1 | 4/2003 | Ito et al. | |
| 2003/0176701 A1 | 9/2003 | Adam et al. | |
| 2003/0216401 A1 | 11/2003 | Bentley et al. | |
| 2004/0024218 A1 | 2/2004 | Barlocco et al. | |

FOREIGN PATENT DOCUMENTS

| | | |
|---|---|---|
| EP | 0 997 464 | 5/2000 |
| EP | 1 122 257 | 8/2001 |
| JP | 10-212290 | 8/1998 |
| JP | 11/228575 | 8/1999 |
| JP | 2000-26466 | 1/2000 |
| JP | 2000-53686 | 2/2000 |
| JP | 2001-39974 | 2/2001 |
| JP | 2001-58991 | 3/2001 |
| WO | 98/54168 | 12/1998 |
| WO | 99/29696 | 6/1999 |
| WO | 99/36421 | 7/1999 |
| WO | 99/48492 | 9/1999 |
| WO | 99/59987 | 11/1999 |
| WO | 00/06545 | 2/2000 |
| WO | 00/08013 | 2/2000 |
| WO | 00/14067 | 3/2000 |
| WO | 00/27815 | 5/2000 |
| WO | 00/31061 | 6/2000 |
| WO | 01/39767 | 6/2001 |
| WO | 01/39775 | 6/2001 |
| WO | 02/10169 | 2/2002 |
| WO | 02/26714 | 4/2002 |
| WO | 02/085291 | 10/2002 |
| WO | 02/085354 | 10/2002 |

(Continued)

OTHER PUBLICATIONS

Francois Jenck, et. al. , "A synthetic agonist at the orphanin FQ/nociceptin receptor ORL1: Anxiolytic profile in the rat" Proceedings of the National Academy of Sciences 2000, 97, 4938-4943.*

(Continued)

*Primary Examiner*—Rita J Desai
*Assistant Examiner*—David K O'Dell
(74) *Attorney, Agent, or Firm*—Wenderoth, Lind & Ponack, L.L.P.

(57) ABSTRACT

The present invention has been made based on the finding that a compound acting on the ORL-1 receptor as an agonist acts as a non-photic entrainment factor, and advances the circadian rhythm phase, and provides a novel therapeutic agent for a sleep disorder such as circadian rhythm sleep disorder, more particularly, an agent for the prophylaxis and/or treatment of a sleep disorder, which contains an ORL-1 receptor agonist, and a novel compound useful as such agent for the prophylaxis and/or treatment.

5 Claims, 4 Drawing Sheets

FOREIGN PATENT DOCUMENTS

| | | |
|---|---|---|
| WO | 02/085355 | 10/2002 |
| WO | 02/085361 | 10/2002 |
| WO | 03/000677 | 1/2003 |

OTHER PUBLICATIONS

Drew Dawson and Stuart Maxwell Amstrong "Chronobiotics-Drugs That Shift Rhythms" Pharmacology and Therapeutics 1996, 69, 15-36.*

Yvan Touitou, André Bogdan "Promoting adjustment of the sleep-wake cycle by chronobiotics" Physiology & Behavior 2007, 90, 294-300.*

Hashiba et. al. "Characterisation and comparison of novel ligands for the nociceptin/orphanin FQ receptor" Naunyn-Schmiedeberg's Archives of Pharmacology, 2001, 363, 28-33.*

Roever et. al. "High-Affinity, Non-Peptide Agonists for the ORL1 (Orphanin FQ/Nociceptin) Receptor" Journal of Medicinal Chemistry 2000, 43, 1329-1338.*

Wichmann, Jurgen et. al. "8-Acenaphthen-1-yl-1-phenyl-1,3,8-triaza-spiro[4.5]decan-4-one derivatives as orphanin FQ receptor agonists." Bioorganic & Medicinal Chemistry Letters, 1999, 9, 2343-2348.*

Laura McAtee et al., "High-Affinity, Non-Peptide Agonists for the ORL1 (Orphanin FQ/Nociceptin) Receptor". CHEMTRACTS—Organic Chemistry, 14(9), pp. 513-517, 2001.

James Bunzow et al., "Molecular cloning and tissue distribution of a putative member of the rat opioid receptor gene family that is not a $\mu$, $\delta$ of $\kappa$ opioid receptor type". FEBS Lett. vol. 347, pp. 284-288, 1994.

Catherine Mollereau et al., "ORL1, a novel member of the opioid receptor family". FEBS Lett. vol. 341, pp. 33-38, 1994.

Jean-Claude Meunier, "Nociceptin/orphanin FQ and the opioid receptor-like ORL1 receptor". European Journal of Pharmacology vol. 340, pp. 1-15, 1997.

Jeffrey S. Mogil et al., "The Molecular and Behavioral Pharmacology of the Orphanin FQ/Nociceptin Peptide and Receptor Family". Pharmacological Reviews, vol. 53, No. 3, pp. 381-415, 2001.

Jean-Claude Meunier et al., "Isolation and structure of the endogenous agonist of opioid receptor-like ORL$_1$ receptor". Letters to Nature, vol. 377, pp. 532-535. 1995.

John Sandin et al., "Short Communication: Nociceptin/Orphanin FQ Microinjected into Hippocampus Impairs Spatial Learning in Rats". European Journal of Neuroscience, vol. 9, pp. 194-197, 1997.

Toshiya Manabe et al., "Facilitation of long-term potentiation and memory in mice lacking nociceptin receptors". Nature, vol. 394, pp. 577-581, 1998.

Francois Jenck et al., "Orphanin FQ acts as an anxiolytic to attenuate behavioral responses to stress". Proc. Natl. Acad. Sci., vol. 94, pp. 14854-14858, 1997.

Anja Koster et al., "Targeted disruption of the orphanin FQ/nociceptin gene increases stress susceptibility and impairs stress adaptation in mice". Proc. Natl. Acad. Sci., vol. 96, pp. 10444-10449, 1999.

Molecular Medicine, vol. 34, No. 3, pp. 355-365, 1997 and partial English translation.

Charles N. Allen, "Orphanin-FQ/Nociceptin (OFQ/N) Modulates the Activity of Suprachiasmatic Nucleus Neurons". The Journal of Neuroscience, vol. 19(6), pp. 2152-2160, 1999.

Rainer K. Reinscheid et al., "Orphanin FQ: A Neuropeptide That Activates an Opioidlike G Protein-Coupled Receptor". Science, vol. 270, pp. 792-794, 1995.

Girolamo Calo et al., "Pharmacology of nociceptin and its receptor: a novel therapeutic target". British Journal of Pharmacology, vol. 129, pp. 1261-1283, 2000.

US 6,172,075, 01/2001, Adam et al. (withdrawn)

* cited by examiner

FIG. 1

- Test compound A
- Test compound B
- Test compound C
- Test compound D

FIG. 2

- Test compound A
- Test compound B
- Test compound C
- Test compound D

REMEDY FOR SLEEP DISTURBANCE

This application is a U.S. national stage of International Application No. PCT/JP03/03925 filed Mar. 28, 2003.

TECHNICAL FIELD

The present invention relates to a medicament useful for treating and/or preventing a sleep disorder. More specifically, the present invention relates to a medicament containing an ORL-1 receptor agonist which is useful for treating and/or preventing a sleep disorder, for example, a circadian rhythm sleep disorder such as jet-lag syndromes, a shift-work sleep disorder, delayed sleep phase syndromes or the like.

BACKGROUND ART

An ORL-1 (opioid receptor-like 1) receptor (FEBS Lett. 347, 284-288, 1994, FEBS Lett. 341, 33-38, 1994) was found to be a fourth opioid receptor next to δ, κ and μ receptors in 1994. The ORL-1 receptor has about 60% homology of amino acid sequences with other opioid receptors, but it is clearly distinguished from other opioid receptors in that naloxone, a non-selective opioid receptor antagonist, does not bind thereto (FEBS Lett. 341, 33-38, 1994). The ORL-1 receptor is mainly distributed in a central nerve system broadly, and is expressed in high density especially in a cerebral cortex, hippocampus, hypothalamus, amygdala and spinal cord, though it is also expressed in peripheral organs such as intestine and spleen (Eur. J. Pharmacol. 340, 1-15, 1997, Pharmacol. Rev. 53, 381-415, 2001).

Endogenous ligands for the ORL-1 receptor were identified successively by the research groups in France and Switzerland in 1995, and were designated as nociceptin (Nature 377, 532-535, 1995) and orphanin FQ (Science 270, 792-794, 1995), respectively. Nociceptin has been reported to be a peptide consisting of 17 amino acids, and plays a critical role in central functions such as learning, memory, anxiety and stress (Br. J. Pharmacol. 129, 1261-1283, 2000).

Specifically, it has been reported that injecting a small amount of nociceptin to hippocampus of rats causes learning disorder in water-maze learning test (Eur. J. Neurosci. 9, 194-197, 1997) and the nociceptin receptor knock-out mice are quick in learning acquisition in water-maze learning test as compared to normal mice (wild-type), and that long term potentiation (LTP) in hippocampus of knock-out mouse is enhanced as compared to normal mice (Nature 394, 577-581, 1998). Nociceptin is considered to inhibit memory and/or learning functions. In addition, it has been reported that if nociceptin is administered intraventricularly in rats, the anti-anxiety activity is found to be almost equivalent to diazepam in a behavioral pharmacology test such as a conflict test, a light-dark box test and an elevated plus maze test (Proc. Natl. Acad. Sci. USA 94, 14854-14858, 1997). Further, it has been reported that the sensitivity to stress is enhanced, and the adaptation ability to stress is inhibited in nociceptin knockout mice as compared to normal mice (Proc. Natl. Acad. Sci. USA 96, 10444-10449, 1999). In other words, nociceptin is considered to have a defensive physiological action against anxiety or stress, and the ORL-1 receptor agonist is likely to show anti-anxiety actions by a completely different mechanism from benzodiazepine compounds.

From the above, it has been reported that a compound having an agonistic and/or antagonistic activity for the ORL-1 receptor, is useful for treating a mental disorder, a neural disorder and a physiological disorder, and in particular for improving anxiety and stress disorders, depression, a trauma disorder, memory loss from Alzheimer's disease or other dementia, epilepsy and spasm symptoms, acute and/or chronic pain symptoms, withdrawal symptoms from drug addiction, control of water balance, $Na^+$ excretion, arterial blood pressure disorder and eating disorder such as obesity and anorexia (publications such as JP-A-2000-26466, JP-A-11-228575, JP-A-10-212290, JP-A-2000-53686, WO00/14067, WO99/29696, EP1122257, JP-A-2001-39974, WO00/08013, WO99/36421, EP0997464, WO03/000677, WO98/54168, WO00/31061, JP-A-2001-58991, WO01/39767, WO01/39775, WO02/085291, WO02/085354, WO02/085355, WO02/085361, WO00/27815, WO00/06545, WO99/59997, WO99/48492, WO02/26714, etc.).

On the other hand, the circadian rhythm sleep disorder is a disease in which a person's main complaint or cardinal symptom is the lack of normal sleep at night, and this disease may sometimes disturb ordinary social behavior. This disease includes a variety of pathological states, for example, endogenous chronic syndromes such as delayed sleep phase syndromes caused by a disruption of the biological clock and its synchronizing mechanism, as well as exogenous acute syndromes such as jet-lag syndromes and a shift-work sleep disorder. Although various drug therapies have been tried for the treatment of circadian rhythm sleep disorder, it has been revealed that only an insufficient therapeutic effect can be obtained with hypnotics, which are typically benzodiazepine hypnotics (as a Review of pathologic states, therapy or others for a circadian rhythm sleep disorder, see, for example, S. Ozaki and K. Okawa, "Sleep Disorder and Biological Rhythm", Special feature; Chronopharmacology, New Guideline of Administration, Molecular Medicine, Vol.34(3), pp. 355-365, 1997, etc.).

Entrainment factors of circadian rhythm are classified into the two major groups of light (photic entrainment) and other factors than light (non-photic entrainment). The drugs which have been known to cause non-photic entrainment so far, are serotonin agonists, benzodiazepine hypnotics, melatonin and the like, but no ORL-1 receptor agonist has been reported to cause non-photic entrainment. One paper has disclosed that a small amount of nociceptin, an endogenous ligand of the ORL-1 receptor, was injected into suprachiasmatic nucleus, biological clock of hamster, but the paper has concluded that nociceptin inhibits photic entrainment, but nociceptin itself does not cause non-photic entrainment (J. Neurosci., Vol.19 (6), pp. 2152-2160, 1999).

In addition, the above-mentioned publications and the patent publication neither disclose nor suggest that a compound having an agonistic and/or antagonistic activity for the ORL-1 receptor, can be used for treating a circadian rhythm sleep disorder.

DISCLOSURE OF THE INVENTION

As described above, the relation of the ORL-1 receptor and the circadian rhythm has not been fully clarified, but the present inventors have found unexpectedly that a compound having an affinity for the ORL-1 receptor, in particular a compound acting on the ORL-1 receptor as an agonist, acts as a non-photic entrainment factor, and advances the circadian rhythm phase. In other words, the present inventors have made extensive researches with the purpose of developing a novel therapeutic agent for circadian rhythm sleep disorder, and have found that ORL-1 receptor agonist can be a preventive and/or therapeutic agent for a sleep disorder including the circadian rhythm sleep disorder, which resulted in the completion of the present invention.

The present invention relates to a medicament useful for treating and/or preventing a sleep disorder. More specifically, the present invention provides a medicament containing an ORL-1 receptor agonist which is useful for preventing and/or treating a sleep disorder, for example, a circadian rhythm sleep disorder such as jet-lag syndromes, a shift-work sleep disorder, or delayed sleep phase syndromes, and a novel compound having an ORL-1 receptor agonist action.

Specifically, the present invention provides the following.
1. A preventive and/or therapeutic agent for a sleep disorder containing an ORL-1 receptor agonist.
2. A preventive and/or therapeutic agent for a sleep disorder comprising a therapeutically effective amount of an ORL-1 receptor agonist and pharmaceutically acceptable additives.
3. The preventive and/or therapeutic agent as described in the above-mentioned 1 or 2, wherein the sleep disorder is a circadian rhythm sleep disorder.
4. The preventive and/or therapeutic agent as described in the above-mentioned 3, wherein the circadian rhythm sleep disorder is a jet-lag syndrome.
5. The preventive and/or therapeutic agent as described in the above-mentioned 3, wherein the circadian rhythm sleep disorder is shift-work sleep disorder.
6. The preventive and/or therapeutic agent as described in the above-mentioned 3, wherein the circadian rhythm sleep disorder is a delayed sleep phase syndrome.
7. The preventive and/or therapeutic agent as described in the above-mentioned 1 or 2, used for preventing and/or treating the symptoms involved in a geriatric circadian rhythm sleep disorder.
8. The preventive and/or therapeutic agent as described in the above-mentioned 1 or 2, used for bright light therapy.
9. The preventive and/or therapeutic agent as described in the above-mentioned 1 or 2, wherein the ORL-1 receptor agonist has an affinity of 1000 nmol/L or less $IC_{50}$ value for the ORL-1 receptor, and further inhibits cAMP elevation caused by a cAMP inducer by 50% or more at a concentration of 1000 nmol/L or less.
10. A compound represented by the formula (I)

wherein
$R^1$ is
(1) hydrogen,
(2) lower alkyl,
(3) lower alkenyl,
(4) —C(O)-lower alkyl,
(5) —C(O)O-lower alkyl,
(6) —C(O)-phenyl (the phenyl group may be substituted with lower alkyl, halogen, lower alkoxy, phenoxy or benzyloxy),
(7) lower alkyl-carboxyl,
(8) lower alkyl-C(O)-phenyl (the phenyl group may be substituted with lower alkyl, halogen, lower alkoxy, phenoxy or benzyloxy),
(9) lower alkyl-C(O)O-lower alkyl,
(10) lower alkenyl-C(O)O-lower alkyl,
(11) lower alkyl-O-lower alkyl,
(12) lower alkyl-C(O)$NR^3R^4$,
(13) —S(O)$_2$-lower alkyl,
(14) —S(O)$_2$-phenyl (the phenyl group may be substituted with lower alkyl, halogen, lower alkoxy, phenoxy or benzyloxy),
(15) lower alkyl-S-lower alkyl,
(16) lower alkyl-S(O)-lower alkyl,
(17) lower alkyl-S(O)$_2$-lower alkyl,
(18) lower alkyl-S(O)$_2NR^3R^4$,
(19) phenyl (the phenyl group may be substituted with lower alkyl, halogen, lower alkoxy, phenoxy or benzyloxy), or
(20) benzyl (the phenyl group may be substituted with lower alkyl, halogen, lower alkoxy, phenoxy or benzyloxy),

$R^2$ is hydrogen, lower alkyl, halogen, lower alkoxy, phenoxy, benzyloxy, trifluoromethyl, nitro, amino or cyano,
$R^3$ and $R^4$ may be the same or different, and each is hydrogen, lower alkyl or lower alkenyl, or $R^3$ and $R^4$ may bind with an adjacent nitrogen atom to form a saturated nitrogen-containing hetero ring (the hetero ring may be substituted with lower alkyl, halogen, lower alkoxy, phenoxy or benzyloxy), and
X is O or S.), a racemic mixture thereof, an enantiomer corresponding thereto, or a pharmaceutically acceptable salt thereof.
11. The compound as described in the above-mentioned 10, wherein $R^2$ is hydrogen, and X is O.
12. The compound as described in the above-mentioned 10, wherein $R^1$ is —C(O)-lower alkyl, lower alkyl-C(O)$NR^3R^4$ (either $R^3$ or $R^4$ is hydrogen) or lower alkyl-C(O)$NR^3R^4$ [$R^3$ and $R^4$ bind with an adjacent nitrogen atom to form a saturated nitrogen-containing hetero ring (the hetero ring may be substituted with lower alkyl, halogen, lower alkoxy, phenoxy or benzyloxy)].
13. The compound as described in the above-mentioned 10, which is selected from
(RS)-1-[1-(acenaphthen-1-yl)piperidin-4-yl]-1,3-dihydro-2H-benzoimidazol-2-one,
(R)-1-[1-(acenaphthen-1-yl)piperidin-4-yl]-1,3-dihydro-2H-benzoimidazol-2-one,
(S)-1-[1-(acenaphthen-1-yl)piperidin-4-yl]-1,3-dihydro-2H-benzoimidazol-2-one,
(R)-3-acetyl-1-[1-(acenaphthen-1-yl)piperidin-4-yl]-1,3-dihydro-2H-benzoimidazol-2-one,
(R)-2-{3-[1-(acenaphthen-1-yl)piperidin-4-yl]-2,3-dihydro-2-oxo-benzoimidazol-1-yl}-N-methylacetamide, and
(R)-1-[1-(acenaphthen-1-yl)piperidin-4-yl]-3-(2-oxo-2-piperazin-1-ylethyl)-1,3-dihydro-2H-benzoimidazol-2-one.
14. The preventive and/or therapeutic agent as described in the above-mentioned 1 or 2, wherein the ORL-1 receptor agonist is a compound represented by the formula (I)

wherein each symbol is as defined above, a racemic mixture thereof, an enantiomer corresponding thereto, or a pharmaceutically acceptable salt thereof.

15. A method of preventing and/or treating a sleep disorder, comprising administering an effective amount of an ORL-1 receptor agonist to the patients.
16. The method as described in the above-mentioned 15, wherein the ORL-1 receptor agonist has an affinity of 1000 nmol/L or less $IC_{50}$ value for ORL-1 receptor, and further inhibits cAMP elevation caused by a cAMP inducer by 50% or more at a concentration of 1000 nmol/L or less.
17. The method as described in the above-mentioned 15, wherein the ORL-1 receptor agonist is a compound represented by the formula (I)

(I)

wherein each symbol is as defined above, a racemic mixture thereof, an enantiomer corresponding thereto, or a pharmaceutically acceptable salt thereof.

18. Use of an ORL-1 receptor agonist for manufacturing a preventive and/or therapeutic agent for a sleep disorder.
19. The use as described in the above-mentioned 18, wherein ORL-1 receptor agonist has an affinity of 1000 nmol/L or less $IC_{50}$ value for ORL-1 receptor, and further inhibits cAMP elevation caused by a cAMP inducer by 50% or more at a concentration of 1000 nmol/L or less.
20. The use as described in the above-mentioned 18, wherein ORL-1 receptor agonist is a compound represented by the formula (I)

(I)

wherein each symbol is as defined above, a racemic mixture thereof, an enantiomer corresponding thereto, or a pharmaceutically acceptable salt thereof.

DETAILED DESCRIPTION OF THE INVENTION

An "ORL-1 receptor agonist" in the present invention refers to a compound having an agonistic activity for an ORL-1 receptor. The ORL-1 receptor agonist is preferably a compound having an affinity of 1000 nmol/L or less $IC_{50}$ value for the ORL-1 receptor, and further inhibits cAMP elevation caused by a cAMP (cyclic adenosine monophosphate) inducer such as forskolin and isoproterenol by 50% or more at a concentration of 1000 nmol/L or less. The present invention comprises both of a full agonist and a partial agonist for the ORL-1 receptor.

Definitions of each symbol in the formula (I) are as follows. In the present specification, the definitions apply irrespective of whether the terms appear alone or in a combination.

"Lower alkyl" means a straight or branched alkyl group containing 1 to 6 carbon atoms, for example, methyl, ethyl, propyl, isopropyl, butyl, isobutyl, secondary butyl, tertiary butyl, pentyl, hexyl and the like. Lower alkyl is preferably a straight or branched alkyl group containing 1 to 4 carbon atoms.

"Lower alkenyl" means, straight or branched alkenyl containing 2 to 6 carbon atoms, for example, vinyl, 1-propenyl, 2-propenyl, isopropenyl, 1-butenyl, 2-butenyl, 3-butenyl and the like. Lower alkenyl is preferably a straight or branched alkenyl group containing 2 to 4 carbon atoms.

"Halogen" means chlorine, iodine, fluorine and bromine. Halogen is preferably fluorine.

"Lower alkoxy" means a straight or branched alkoxy group containing 1 to 6 carbon atoms, for example, methoxy, ethoxy, propoxy, isopropoxy, butoxy and the like. Lower alkoxy is preferably a straight or branched alkoxy group containing 1 to 4 carbon atoms.

A "saturated nitrogen-containing hetero ring formed by binding with an adjacent nitrogen atom", means a 5- or 6-membered ring which may further contain 1 to 3 heteroatoms selected from a nitrogen atom, an oxygen atom and a sulfur atom, for example, piperidine, pyrrolidine, morpholine, thiomorpholine, piperadine, methyl piperadine and the like. Piperadine and morpholine are preferred.

"—C(O)—" means a carbonyl group.
"—S(O)—" means a sulfinyl group.
"—S(O)$_2$—" means a sulfonyl group.

A "pharmaceutically acceptable salt" comprises an acid-addition salt with an inorganic acid and an organic acid such as chloric acid, oxalic acid, fumaric acid and the like, and a salt with an inorganic base such as sodium, potassium, calcium, magnesium and the like.

If the phenyl group and the saturated nitrogen-containing hetero ring formed by binding with an adjacent nitrogen atom in the formula (I) are substituted with lower alkyl, halogen, lower alkoxy, phenoxy or benzyloxy, the number of the substituent is preferably 1 to 3.

The compound is preferably a compound wherein $R^1$ is hydrogen, lower alkyl, —C(O)-lower alkyl, lower alkyl-carboxyl, lower alkyl-C(O)O-lower alkyl or lower alkyl-C(O)NR$^3$R$^4$, or —S(O)$_2$-lower alkyl, $R^2$ is hydrogen or halogen, $R^3$ and $R^4$ are hydrogen or lower alkyl, or $R^3$ and $R^4$ bind with an adjacent nitrogen atom to form a saturated nitrogen-containing hetero ring (the hetero ring may be substituted with lower alkyl, halogen, lower alkoxy, phenoxy or benzyloxy), and X is O or S. Examples of preferred compound are as follows.

[1] (RS)-1-[1-(acenaphthen-1-yl)piperidin-4-yl]-1,3-dihydro-2H-benzoimidazol-2-one,
[2] (RS)-1-[1-(acenaphthen-1-yl)piperidin-4-yl]-1,3-dihydro-5-fluoro-2H-benzoimidazol-2-one,
[3] (RS)-1-[1-(acenaphthen-1-yl)piperidin-4-yl]-1,3-dihydro-6-fluoro-2H-benzoimidazol-2-one,
[4] ethyl (RS)-2-{3-[1-(acenaphthen-1-yl)piperidin-4-yl]-2,3-dihydro-2-oxo-benzoimidazol-1-yl}acetate,
[5] (RS)-2-{3-[1-(acenaphthen-1-yl)piperidin-4-yl]-2,3-dihydro-2-oxo-benzoimidazol-1-yl}acetic acid,
[6] (RS)-1-[1-(acenaphthen-1-yl)piperidin-4-yl]-3-(2-oxo-2-piperazin-1-ylethyl)-1,3-dihydro-2H-benzoimidazol-2-one dihydrochloride,
[7] (RS)-1-[1-(acenaphthen-1-yl)piperidin-4-yl]-3-[2-(4-methylpiperazin-1-yl)-2-oxoethyl]-1,3-dihydro-2H-benzoimidazol-2-one dihydrochloride,
[8] (RS)-1-[1-(acenaphthen-1-yl)piperidin-4-yl]-3-(2-morpholin-4-yl-2-oxoethyl)-1,3-dihydro-2H-benzoimidazol-2-one hydrochloride,
[9] (RS)-1-[1-(acenaphthen-1-yl)piperidin-4-yl]-1,3-dihydro-2H-benzoimidazole-2-thione,
[10] (RS)-1-[1-(acenaphthen-1-yl)piperidin-4-yl]-1,3-dihydro-3-methyl-2H-benzoimidazole-2-thione,
[11] (R)-1-[1-(acenaphthen-1-yl)piperidin-4-yl]-1,3-dihydro-2H-benzoimidazol-2-one,
[12] (S)-1-[1-(acenaphthen-1-yl)piperidin-4-yl]-1,3-dihydro-2H-benzoimidazol-2-one,
[13] (R)-3-acetyl-1-[1-(acenaphthen-1-yl)piperidin-4-yl]-1,3-dihydro-2H-benzoimidazol-2-one,
[14] (R)-1-[1-(acenaphthen-1-yl)piperidin-4-yl]-3-methanesulfonyl-1,3-dihydro-2H-benzoimidazol-2-one,
[15] ethyl (R)-2-(3-[1-(acenaphthen-1-yl)piperidin-4-yl]-2,3-dihydro-2-oxo-benzoimidazol-1-yl)acetate,
[16] (R)-2-{3-[1-(acenaphthen-1-yl)piperidin-4-yl]-2,3-dihydro-2-oxo-benzoimidazol-1-yl}acetic acid,
[17] (R)-1-[1-(acenaphthen-1-yl)piperidin-4-yl]-3-(2-oxo-2-piperazin-1-ylethyl)-1,3-dihydro-2H-benzoimidazol-2-one dihydrochloride,
[18] (R)-2-{3-[1-(acenaphthen-1-yl)piperidin-4-yl]-2,3-dihydro-2-oxo-benzoimidazol-1-yl}-N-methylacetamide,
[19] (R)-2-{3-[1-(acenaphthen-1-yl)piperidin-4-yl]-2,3-dihydro-2-oxo-benzoimidazol-1-yl}-N,N-dimethylacetamide, and
[20] (R)-2-{3-[1-(acenaphthen-1-yl)piperidin-4-yl]-2,3-dihydro-2-oxo-benzoimidazol-1-yl}acetamide.

Particularly preferred compound is a compound wherein $R^1$ is hydrogen, —C(O)-lower alkyl or lower alkyl-C(O)$NR^3R^4$ (either $R^3$ or $R^4$ is hydrogen) or lower alkyl-C(O)$NR^3R^4$ ($R^3$ and $R^4$ bind with an adjacent nitrogen atom to form a saturated nitrogen-containing hetero ring (the hetero ring may be substituted with lower alkyl, halogen, lower alkoxy, phenoxy or benzyloxy)), $R^2$ is hydrogen and X is O. Examples of especially preferred compound are as follows.
(RS)-1-[1-(acenaphthen-1-yl)piperidin-4-yl]-1,3-dihydro-2H-benzoimidazol-2-one,
(R)-1-[1-(acenaphthen-1-yl)piperidin-4-yl]-1,3-dihydro-2H-benzoimidazol-2-one,
(S)-1-[1-(acenaphthen-1-yl)piperidin-4-yl]-1,3-dihydro-2H-benzoimidazol-2-one,
(R)-3-acetyl-1-[1-(acenaphthen-1-yl)piperidin-4-yl]-1,3-dihydro-2H-benzoimidazol-2-one,
(R)-2-{3-[1-(acenaphthen-1-yl)piperidin-4-yl]-2,3-dihydro-2-oxo-benzoimidazol-1-yl}-N-methylacetamide, and
(R)-1-[1-(acenaphthen-1-yl)piperidin-4-yl]-3-(2-oxo-2-piperadin-1-ylethyl)-1,3-dihydro-2H-benzoimidazol-2-one.

The compound of the formula (I) can be prepared, for example, by the following methods.

Method 1 wherein each symbol is as defined above.

A compound of the formula (II) is reductively aminated by a compound of the formula (III) to obtain a compound of the formula (I). The compound of the formula (II) and the compound of the formula (III) are known compounds. The compound of the formula (II) can be prepared by the method described in J. Chem. Soc., Perkin Trans 1, 1160, 1973, and the compound of the formula (III) can be prepared by the method described in J. Med. Chem., 2001, 44, 3378.

Reductive amination of a keto compound of the formula (II) with amine such as the compound of the formula (III) is described in J. Org. Chem., 55, 2552-54, 1990. The present reaction according to this method is carried out by reacting ketone with amine in the presence of Ti(IV)-isopropoxide and sodium cyanoborohydride in a solvent such as tetrahydrofuran(THF), methanol or ethanol, or a mixture of suitable alcohol and THF. The reaction temperature is about −78 to 100° C., and the reaction time is dozens of minutes to 2 days.

Method 2 wherein each symbol is as defined above.

The compound of the formula (I-1) wherein $R^1$ is hydrogen, is subjected to alkylation, alkenylation, phenylation, benzylation or acylation to prepare a compound of the formula (I).

The compound of the formula (I-1) wherein R is hydrogen, can be subjected to alkylation, alkenylation, phenylation, benzylation or acylation according to a conventional method, for example, in the presence of corresponding alkyl-halide, alkenyl-halide, benzyl-halide or acyl-halide such as methyl iodide, allyl bromide, benzyl bromide, ethyl bromide, acetyl chloride and ethyl bromoacetate. This reaction is carried out in the presence of metal hydride such as sodium hydride at a temperature of about −78 to 100° C. for a reaction time of dozens of minutes to 2 days.

wherein each symbol is as defined above.

The compound of the formula (IV) is treated with phenylene diamine represented by the formula (V) to produce a compound of the formula (VI), which is cyclized to obtain a compound of the formula (I-1) wherein $R^1$ is hydrogen.

Reductive amination of a keto compound of the formula (IV) with phenylene diamine of the formula (V) is carried out in the presence of a metal hydride complex (for example, sodium triacetoxy borohydride, sodium cyanoborohydride, sodium borohydride, lithium borohydride and lithium aluminum hydride) in N,N-dimethylformamide, dimethylsulfoxide, pyridine, dioxane, tetrahydrofuran, acetonitrile, chloroform, methylene chloride, dichloroethane, methanol, ethanol, diethyl ether and the like, or a mixed solvent thereof. The reaction temperature is about −78 to 100° C., and the reaction time is dozens of minutes to 2 days. In addition, phenylene diamine of the formula (V) and the keto compound of the formula (IV) are known compounds. For example, phenylene diamine of the formula (V) can be prepared by the method described in J. Org. Chem., 2001, 66, 919 or in Org. Synth., 1943, 501, and the keto compound of the formula (IV) can be prepared by the method described in Bioorganic & Medicinal Chemistry Letters, 1999, 9, 2343.

The compound of the formula (VI) prepared in the present reaction can be carbonylated or thiocarbonylated by a known method (See, Bioorganic & Medicinal Chemistry Letters, 1996, 6, 1641, Chem. Pharm. Bull., 1989, 37, 962, Bioorganic & Medicinal Chemistry Letters, 1999, 9, 1537, etc.) to produce a compound of the formula (I-1).

wherein $R^{11}$ is lower alkyl-carboxyl and $R^{12}$ is lower alkyl-$C(O)NR^3R^4$. $R^3$, $R^4$ and X are as defined above.

A carbonic acid compound represented by the formula (I-2) or a reactive derivative thereof is reacted with amine to obtain a compound of the formula (I-3). The reactive derivative of a carbonic acid compound includes acid halide such as acid chloride, acid anhydride, mixed acid anhydride formed from ethyl chloroformate and the like, ester such as methyl ester and ethyl ester and a reactive derivative formed from carbodiimide such as WSC.HCl (water soluble carbodiimide hydrochloride) and DCC (dicyclohexyl carbodiimide), and the like. The reaction is carried out in an organic solvent such as N,N-dimethylformamide, dimethylsulfoxide, dioxane, tetrahydrofuran, acetonitrile, chloroform, methylene chloride, dichloroethane and toluene. The reaction temperature is about −78 to 100° C., and the reaction time is dozens of minutes to 2 days. Further, if necessary, an organic base such as pyridine, triethylamine and diisopropylethylamine is used as a deoxidizer.

Thus-synthesized compound of the formula (I) can be obtained as a racemate, and the racemic mixture can be converted to an enantiomer component thereof to produce an optically pure compound.

In addition, enantiomer of the compound of the formula (I) can be also produced by using optically active materials.

If necessary, the obtained compound of the formula (I) is converted to a pharmaceutically acceptable salt. The salt formation is per se known, and further carried out by well-known method at room temperature. A salt with an organic acid is also considered as well as salt with inorganic acid, and for a compound having a carboxyl group, salt with inorganic base is also considered. Examples of such salt are an acid-addition salt such as hydrochloride, oxalate and a fumarate, a sodium salt, a potassium salt, a calcium salt, a magnesium salt and the like.

The ORL-1 receptor agonist which is an active ingredient of a preventive and/or therapeutic agent for a sleep disorder of the present invention is not limited if it has agonistic activity for the ORL-1 receptor, but is preferably a compound having an affinity of 1000 nmol/L or less $IC_{50}$ value for an ORL-1 receptor, and further inhibits cAMP elevation caused by a cAMP inducer by 50% or more at a concentration of 1000 nmol/L or less. Examples of the cAMP inducer include forskolin and isoproterenol.

The compound having an agonistic activity for the ORL-1 receptor is preferably the compound of the formula (I), but also includes the compound having an agonistic activity for the ORL-1 receptor among the piperidine compounds or the amide compounds disclosed in publications such as JP-A-2000-26466, JP-A-11-228575, JP-A-10-212290, JP-A-2000-53686, WO00/14067, WO99/29696, EP1122257, JP-A-2001-39974, WO00/08013, WO99/36421, EP0997464, WO98/54168, WO00/31061, JP-A-2001-58991, WO01/39767, WO01/39775, WO02/085291, WO02/085354, WO02/085355, WO02/085361, WO00/27815, WO00/06545, WO99/59997, WO99/48492, WO02/26714 and WO03/000677. The "ORL-1 receptor agonist" in the present invention also includes ORL-1 receptor agonist compounds described in these publications.

Among these, specific examples are
(RS)-8-(acenaphthen-1-yl)-1-phenyl-1,3,8-triazaspiro[4.5]decan-4-one,
8-(decahydro-naphthalen-2-yl)-3-methyl-1-phenyl-1,3,8-triazaspiro[4.5]decan-4-one,
(1S,3aS)-8-(2,3,3a,4,5,6-hexahydro-1H-phenalene-1-yl)-1-phenyl-1,3,8-triazaspiro[4.5]decan-4-one,
1-(1-cyclooctylmethyl-4-piperidinyl)-2-(4-methylpiperadinyl)-1H-benzoimidazole and the like though the chemical structure is not especially limited.

The effects of the present invention will be explained in detail in the section of pharmacological tests below. The present inventors have investigated at first if compounds having various chemical structures have an agonistic and/or antagonistic activity for the ORL-1 receptor, and then have administered compounds having an agonistic or antagonistic activity for the ORL-1 receptor to rats, and as results, they have found that a compound having an ORL-1 receptor agonistic activity also showed the phase advancing effect.

Since the present invention is characterized by the findings that an ORL-1 receptor agonist shows the phase advancing effect regardless of the chemical structure, the strength of their effects does not affect the usefulness of the present invention.

The sleep disorder which is the subject for the preventive and/or therapeutic agent of the present invention includes, for example, a circadian rhythm sleep disorder such as jet-lag syndromes, a shift-work sleep disorder, or delayed sleep phase syndromes. The circadian rhythm sleep disorder also includes the disorder peculiar to the elders (a geriatric circadian rhythm sleep disorder).

In addition, the preventive and/or therapeutic agent of the present invention can be used suitably for a bright light therapy.

A compound having an ORL-1 receptor agonistic activity (an ORL-1 receptor agonist) in the present invention can be administered orally or non-orally. Dosage form includes tablet, capsule, granule, powder, injection, ointment, and suppository and the like. These can be formulated by generally used techniques combining the ORL-1 receptor agonist and various pharmaceutically acceptable additives (an excipient, a diluent, a lubricant, a binder, a disintegrant, a coating agent, a filming agent, a base, a solvent, etc.). For example, an oral formulation such as a tablet, a capsule, a granule and a powder can be prepared using a diluent such as lactose, crystalline cellulose, starch and vegetable oil, a lubricant such as magnesium stearate and talc, a binder such as hydroxypropyl cellulose and polyvinyl pyrrolidone, a disintegrant such as carboxymethyl cellulose calcium and low-substituted hydroxypropylmethyl cellulose, a coating agent such as hydroxypropylmethylcellulose, macrogol and silicone resin, a filming agent such as gelatin film, as desired. An ointment can be prepared using a commonly used base such as white Vaseline and liquid paraffin.

The amount of an ORL-1 receptor agonist, an active ingredient in these formulations is 0.1 to 100% by weight, suitably 1 to 50% by weight. In addition, the dose may be suitably selected depending on symptoms, age, dosage form and the like. For the oral formulation, the dose is usually 0.1 to 5000 mg, preferably, 1 to 1000 mg per day and may be administered in a single dose or divided doses.

In addition, the present invention provides a commercial package comprising the above-described preventive and/or therapeutic agent containing an ORL-1 receptor agonist, and a document describing that the preventive and/or therapeutic agent can be or should be used for preventing and/or treating a sleep disorder.

The results of Examples, Formulation Examples and Pharmacological Examples are shown in the following. These are for better understanding of the present invention and do not limit the scope of the present invention.

EXAMPLE 1

(RS)-1-[1-(acenaphthen-1-yl)piperidin-4-yl]-1,3-dihydro-2H-benzoimidazol-2-one (1) 1-Naphthylacetic acid (100 g, 530 mmol) was dissolved in dichloromethane (15 ml). Thionyl chloride (158 g, 1.32 mol) was added under ice-cooling and the mixture was heated under reflux for 1 hr. The solvent was evaporated and 1,2-dichloroethane (500 ml) was added to the obtained residue for dissolution. Aluminum chloride (150 g, 1.12 mol) was added under ice-cooling, and the mixture was stirred at room temperature for 1 hr. The reaction mixture was poured into ice water, and the mixture was extracted with dichloromethane. The extract was washed with water and saturated brine, dried over magnesium sulfate and concentrated to give acenaphthen-1-one (80 g) as yellow crystals.

$^1$H-NMR(CDCl$_3$)$\delta_{TMS}$: 3.79(s, 2H), 7.43(d, J=6.8 Hz, 1H), 7.57(t, J=6.8 Hz, 1H), 7.68(t, J=7.5 Hz, 1H), 7.79(d, J=6.8 Hz, 1H), 7.93(d, J=6.8 Hz, 1H), 8.06(d, J=6.8 Hz, 1H)

FAB-MS(M+H)$^+$: 169

(2) Acenaphthen-1-one (1.68 g, 10 mmol) was dissolved in tetrahydrofuran (THF, 15 ml). 4-(2-Keto-1-benzoimidazolinyl)piperidine (2.17 g, 10 mmol) and tetraisopropyl orthotitanate (3.4 g, 12 mmol) were added and the mixture was stirred at room temperature for 20 hr. The solvent was evaporated and a mixed solvent (15 ml) of THF/ethanol (1:2) was added to the obtained residue for dissolution. Sodium cyanoborohydrate (2.1 mmol) was added to this solution, and the mixture was stirred at stirred at room temperature for one day. Water was added, and the precipitate was removed by celite filtration and washed with ethanol. The filtrate was extracted with chloroform and washed with water and saturated brine. The extract was dried over sodium sulfate, and concentrated. The obtained residue was purified by silica gel column chromatography (chloroform/methanol) to give the title compound (0.68 g) as yellow crystals.

$^1$H-NMR(CDCl$_3$)$\delta_{TMS}$: 1.74-1.82(m, 2H), 2.36-2.60(m, 4H), 2.81(m, 1H), 3.01(m, 1H), 3.42(d, J=5.6 Hz, 2H), 4.29-4.36(m, 1H), 4.98(t, J=5.6 Hz, 1H), 7.01(m, 3H), 7.28-7.31(m, 2H), 7.43-7.53(m, 3H), 7.60-7.62(m, 1H), 7.69(m, 1H), 9.77(brs, 1H)

FAB-MS(M+H)$^+$: 370

EXAMPLE 2

(RS)-1-[1-(acenaphthen-1-yl)piperidin-4-yl]-1,3-dihydro-5-fluoro-2H-benzoimidazol-2-one The title compound was obtained as pale-yellow crystals according to Example 1 and using 4-(5-fluoro-2-keto-1-benzoimidazolinyl)piperidine.

$^1$H-NMR(CDCl$_3$)$\delta_{TMS}$: 1.72-1.85(m, 2H), 2.38-2.56(m, 4H), 2.86(m, 1H), 3.11(m, 1H), 3.42(d, J=5.6 Hz, 2H), 4.30-4.36(m, 1H), 4.98(t, J=5.6 Hz, 1H), 6.68(dd, J=13.2, 7.8 Hz, 1H), 7.28-7.31(m, 2H), 7.46-7.53(m, 3H), 7.60(d, J=7.8 Hz, 1H), 7.62(m, 1H), 7.69(m, 1H), 9.66(brs, 1H)

FAB-MS(M+H)$^+$: 388

EXAMPLE 3

(RS)-1-[1-(acenaphthen-1-yl)piperidin-4-yl]-1,3-dihydro-6-fluoro-2H-benzoimidazol-2-one The title compound was obtained as pale-yellow crystals according to Example 1 and using 4-(6-fluoro-2-keto-1-benzoimidazolinyl)piperidine.

$^1$H-NMR(CDCl$_3$)$\delta_{TMS}$: 1.72-1.86(m, 2H), 2.36-2.54(m, 4H), 2.88(m, 1H), 3.11(m, 1H), 3.42(d, J=5.6 Hz, 2H), 4.32-4.38(m, 1H), 4.96(t, J=5.6 Hz, 1H), 6.72(dd, J=13.2, 7.8 Hz, 1H), 7.33-7.36(m, 2H), 7.46-7.53(m, 3H), 7.60(d, J=7.8 Hz, 1H), 7.62(m, 1H), 7.69(m, 1H), 9.78(brs, 1H)

FAB-MS(M+H)$^+$: 388

EXAMPLE 4

Ethyl (RS)-2-{3-[1-(acenaphthen-1-yl)piperidin-4-yl]-2,3-dihydro-2-oxo-benzoimidazol-1-yl}acetate (RS)-1-[1-(Acenaphthen-1-yl)piperidin-4-yl]-1,3-dihydro-2H-benzoimidazol-2-one (1.5 g, 4 mmol) was dissolved in dimethylformamide (DMF, 15 ml). Sodium hydride (200 mg, 60%) was added and the suspension was stirred at 50° C. for 30 min. The mixture was cooled to room temperature, ethyl bromoacetate (0.75 g, 4.5 mmol) was added and the mixture was stirred for 1 hr. The reaction mixture was poured into water and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give the title compound (1.6 g) as pale-yellow crystals.

$^1$H-NMR(CDCl$_3$)$\delta_{TMS}$: 1.25(t, J=7.1, 3H), 1.82(m, 2H), 2.42-2.58(m, 4H), 2.78(m, 1H), 3.03((m, 1H), 3.44(m, 2H), 4.22(q, J=7.1 Hz, 2H), 4.35(m, 1H), 4.61(s, 2H), 5.01(m, 1H), 6.87(m, 1H), 7.05(m, 2H), 7.31(m, 2H), 7.45-7.55(m, 3H), 7.63(m, 1H), 7.71(m, 1H)

FAB-MS(M+H)$^+$: 456

EXAMPLE 5

(RS)-2-{3-[1-(acenaphthen-1-yl)piperidin-4-yl]-2,3-dihydro-2-oxo-benzoimidazol-1-yl}acetic Acid Ethyl (RS)-2-{3-[1-(acenaphthen-1-yl)piperidin-4-yl]-2,3-dihydro-2-oxo-benzoimidazol-1-yl}acetate (1.6 g) was dissolved in ethanol (10 ml) and 2N-aqueous sodium hydroxide solution (10 ml) was added. The mixture was stirred at room temperature for 30 min. The reaction mixture was poured into water, thereto was added to 1N-hydrochloric acid for neutralization, and the mixture was extracted with chloroform. The extract was washed with water and saturated brine, dried over magnesium sulfate, and concentrated. The obtained solid was washed with ethyl acetate to give the title compound (1.3 g) as pale-yellow crystals.

$^1$H-NMR(DMSO-d$_6$)$\delta_{TMS}$: 1.72-1.83(m, 2H), 2.63-3.12 (m, 5H), 3.30(m, 1H), 3.50-3.70(m, 2H), 4.49(m, 1H), 4.58(s, 2H), 5.36(m, 1H), 7.02-7.13(m, 2H), 7.14(d, J=6.8 Hz, 1H), 7.40(d, J=6.8 Hz, 1H), 7.52-7.65(m, 3H), 7.72(d, J=8.3 Hz, 1H), 7.84(d, J=8.3 Hz, 1H), 8.31(m, 1H), 11.55(brs, 1H)

FAB-MS(M+H)$^+$: 428

EXAMPLE 6

(RS)-1-[1-(acenaphthen-1-yl)piperidin-4-yl]-3-(2-oxo-2-piperazin-1-ylethyl)-1,3-dihydro-2H-benzoimidazol-2-one dihydrochloride (1) (RS)-2-{3-[1-(Acenaphthen-1-yl)piperidin-4-yl]-2,3-dihydro-2-oxo-benzoimidazol-1-yl}acetic acid (0.85 g, 2 mmol) was dissolved in DMF (10 ml). Boc-piperazine (tert-butoxycarbonylpiperazine) (0.37 g, 2 mmol), WSC.HCl (water soluble carbodiimide hydrochloric acid) (0.46 g, 2.4 mmol), HOBt (hydroxybenzotriazole) (0.37 g, 2.4 mmol) and triethylamine (0.53 ml, 3.8 mmol) were added and the mixture was stirred at room temperature for 10 hr. The reaction mixture was poured into water, and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give a yellow solid (0.8 g).

(2) The above-mentioned yellow solid (0.8 g) was dissolved in 4N-hydrochloric acid/dioxane (10 ml) and the mixture was stirred at room temperature for 1 hr. The solvent was evaporated and isopropyl ether was added to the residue. The obtained crystals were collected by filtration to give the title compound (0.5 g) as yellow crystals.

$^1$H-NMR(DMSO-d$_6$)$\delta_{TMS}$: 1.76-1.88(m, 2H), 3.11-3.82 (m, 15H), 3.96(m, 1H), 4.71(m, 1H), 4.83(s, 2H), 5.63(m, 1H), 7.02-7.12(m, 3H), 7.46(d, J=6.8 Hz, 1H), 7.58(t, J=8.0 Hz, 1H), 7.67(t, J=7.8 Hz, 1H), 7.76-7.84(m, 2H), 7.92(m, 1H), 8.25(d, J=7.8 Hz, 1H), 9.42(brs, 2H), 12.20(brs, 1H)

FAB-MS(M+H)$^+$: 496

EXAMPLE 7

(RS)-1-[1-(acenaphthen-1-yl)piperidin-4-yl]-3-[2-(4-methylpiperazin-1-yl)-2-oxoethyl]-1,3-dihydro-2H-benzoimidazol-2-one dihydrochloride (RS)-2-{3-[1-(Acenaphthen-1-yl)piperidin-4-yl]-2,3-dihydro-2-oxo-benzoimidazol-1-yl}acetic acid (0.85 g, 2 mmol) was dissolved in DMF (10 ml). 1-Methylpiperazine (0.2 g, 2 mmol), WSC.HCl (0.46 g, 2.4 mmol), HOBt (0.37 g, 2.4 mmol) and triethylamine (0.53 ml, 3.8 mmol) were added and the mixture was stirred at room temperature for 8 hr. The reaction mixture was poured into water, and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) and hydrochloric acid/ethanol was added to give the title compound (0.73 g) as a yellow solid.

$^1$H-NMR(DMSO-d$_6$)$\delta_{TMS}$: 1.76-1.89(m, 2H), 2.77-3.74 (m, 16H), 3.96(m, 1H), 4.16(m, 1H), 4.31(m, 1H), 4.71(m, 1H), 4.76(d, J=17.3 Hz, 1H), 4.92(d, J=17.3 Hz, 1H), 5.63(m, 1H), 7.02-7.09(m, 3H), 7.45-7.55(m, 1H), 7.56-7.65(m, 1H), 7.67-7.69(m, 1H), 7.76-7.82(m, 2H), 7.91-7.94(m, 1H), 8.25 (m, 1H), 11.32(brs, 1H), 12.23(brs, 1H)

FAB-MS(M+H)$^+$: 510

EXAMPLE 8

(RS)-1-[1-(acenaphthen-1-yl)piperidin-4-yl]-3-(2-morpholin-4-yl-2-oxoethyl)-1,3-dihydro-2H-benzoimidazol-2-one hydrochloride The title compound was obtained as pale-yellow crystals according to Example 7 and using morpholine.

$^1$H-NMR(DMSO-d$_6$)δ$_{TMS}$: 1.78-1.89(m, 2H), 2.83(m, 1H), 3.05(m, 2H), 3.31-3.76(m, 12H), 3.95(m, 1H), 4.69(m, 1H), 4.76(s, 2H), 5.63(m, 1H), 7.02-7.08(m, 3H), 7.45-7.47 (m, 1H), 7.56-7.60(m, 1H), 7.66-7.78(m, 3H), 7.92-7.94(m, 1H), 8.18(m, 1H), 11.85(brs, 1H)

FAB-MS(M+H)$^+$: 497

EXAMPLE 9

(RS)-1-[1-(acenaphthen-1-yl)piperidin-4-yl]-1,3-dihydro-2H-benzoimidazole-2-thione (1) Acenaphthen-1-one (34 g, 200 mmol) was dissolved in methanol (300 ml). Sodium borohydride (8 g, 200 mmol) was added to this solution under ice-cooling, and the mixture was stirred at room temperature for 1 hr. The reaction mixture was poured into water, and the mixture was extracted with ethyl acetate. The extract was washed with water and saturated brine, dried over magnesium sulfate, and concentrated to give 1-acenaphthenol (33 g) as yellow crystals.

(2) To a solution of 1-acenaphthenol (33 g, 190 mmol) and diphenylphosphorylazide (63 g, 230 mmol) in toluene (300 ml) was cooled to 0° C., DBU (diazabicycloundecene) (35 g, 230 mmol) was added and the mixture was stirred at room temperature for 6 hr. The reaction mixture was poured into water and extracted with toluene. The combined organic phase was washed with water, dried over magnesium sulfate, and concentrated. A crude product was dissolved in a mixed solvent (330 ml) of THF/water (10:1), triphenylphosphine (53 g) was added thereto, and the mixture was heated under reflux for 6 hr. After cooling to room temperature, the solvent was evaporated and 1N-hydrochloric acid (200 ml) was added to the residue. Unnecessary materials were extracted with ethyl acetate. The aqueous phase was alkalified with potassium carbonate and extracted with chloroform. The extract was washed with water and saturated brine, dried over magnesium sulfate, and concentrated to give acenaphthen-1-yl-amine (20 g) as a red oil.

(3) Acenaphthen-1-yl-amine (20 g, 118 mmol) was dissolved in ethanol (200 ml). Potassium carbonate (1.7 g, 12 mmol) and 1-ethyl-1-methyl-4-oxopiperidinium iodide (38 g) dissolved in water (100 ml) was added and the mixture was heated under reflux for 1 hr. The reaction mixture was poured into water, and the mixture was extracted with ethyl acetate. The extract was washed with water and saturated brine, dried over magnesium sulfate, and concentrated. The obtained residue was purified by silica gel column chromatography (chloroform/methanol) to give 1-(acenaphthen-1-yl)-piperidin-4-one (23 g) as yellow crystals.

(4) To a solution of 1-(acenaphthen-1-yl)-piperidin-4-one (12 g, 48 mmol) and 1,2-phenylenediamine (10.8 g, 100 mmol) in THF (100 ml) was cooled to 0° C. were added sodium triacetoxy borohydride (34 g) and acetic acid (12 ml) and the mixture was stirred at room temperature for 17 hr. The reaction mixture was poured into water and potassium carbonate was added for neutralization. The mixture was extracted with ethyl acetate. The extract was washed with water and saturated brine, dried over sodium sulfate, and concentrated. The obtained residue was purified by silica gel column chromatography (chloroform/methanol) to give N-[1-(acenaphthen-1-yl)piperidin-4-yl]-benzene-1,2-diamine (8.5 g) as yellow crystals.

(5) N-[1-(Acenaphthen-1-yl)piperidin-4-yl]-benzene-1,2-diamine (1 g, 3 mmol) was dissolved in THF (30 ml), and triethylamine (1.4 ml, 10 mmol) and 1,1'-thiocarbonyldiimidazole (0.63 g, 3.5 mmol) were added. The mixture was stirred at room temperature for 3 hr. The reaction mixture was poured into water, and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give the title compound (1.17 g) as a gray-white solid.

$^1$H-NMR(CDCl$_3$)δ$_{TMS}$: 1.85(m, 2H), 2.42-2.55(m, 3H), 2.63(m, 1H), 2.82(m, 1H), 3.04(m, 1H), 3.44(d, J=5.6 Hz, 2H), 4.98(t, J=5.6 Hz, 1H), 5.19(m, 1H), 7.15-7.24(m, 3H), 7.29(m, 1H), 7.45(m, 1H), 7.50-7.63(m, 4H), 7.68(m, 1H), 9.62(brs, 1H)

FAB-MS(M+H)$^+$: 386

EXAMPLE 10

(RS)-1-[1-(acenaphthen-1-yl)piperidin-4-yl]-1,3-dihydro-3-methyl-2H-benzoimidazole-2-thione (RS)-1-[1-(Acenaphthen-1-yl)piperidin-4-yl]-1,3-dihydro-2H-benzoimidazole-2-thione (1 g, 2.6 mmol) was dissolved in DMF (15 ml) and sodium hydride (120 mg, 60%) was added. The suspension was stirred at 50° C. for 30 min. After cooling to room temperature, methyl iodide (0.4 g, 2.8 mmol) was added and the mixture was stirred for 1 hr. The reaction mixture was poured into water, and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give the title compound (1.05 g) as pale-yellow crystals.

$^1$H-NMR(CDCl$_3$)δ$_{TMS}$: 1.83(m, 2H), 2.38(m, 1H), 2.51-2.64(m, 3H), 2.78(s, 3H), 2.83(m, 1H), 3.05(m, 1H), 3.45(d, J=5.6 Hz, 2H), 4.15(m, 1H), 5.01(t, J=5.6 Hz, 1H), 7.15-7.21 (m, 2H), 7.31(m, 1H), 7.47(m, 1H), 7.54-7.73(m, 6H)

FAB-MS(M+H)$^+$: 400

EXAMPLE 11

(R)-1-[1-(acenaphthen-1-yl)piperidin-4-yl]-1,3-dihydro-2H-benzoimidazol-2-one (1) (R)-2-Methyl-CBS-oxazaboro-lidine (50 ml, 1 mol toluene solution) was cooled to −30° C., and a borane.THF complex (250 ml, 1 mol THF solution) was added. The mixture was stirred for 45 min. Acenaphthen-1-one (40 g, 240 mmol) was dissolved in dichloromethane (500 ml) and the solution was added dropwise. The mixture was stirred under cooling (−30° C.) for 2 hr. Then, methanol (80 ml) and 1N-hydrochloric acid (100 ml) were added under ice-cooling, and the mixture was extracted with ethyl acetate. The extract was washed with water and saturated aqueous ammonium chloride solution, dried over magnesium sulfate, and concentrated to give (S)-1-acenaphthenol (35 g) as pale-yellow crystals.

$^1$H-NMR(CDCl$_3$)$\delta_{TMS}$: 1.96(brs, 1H), 3.24(d, J=17.5 Hz, 1H), 3.80(dd, J=17.5, 7.5 Hz, 1H), 5.73(m, 1H), 7.30(d, J=6.8 Hz, 1H), 7.48(t, J=6.8 Hz, 1H), 7.53-7.56(m, 2H), 7.64(d, J=7.5 Hz, 1H), 7.75(m, 1H)

FAB-MS(M+H)$^+$: 171

$[\alpha]_D^{20}$=1.93

(2) A solution of (S)-1-acenaphthenol (35 g, 200 mmol) and diphenylphosphorylazide (66 g, 240 mmol) in toluene (300 ml) was cooled to 0° C. and DBU (36 g, 240 mmol) was added. The mixture was stirred at room temperature for 6 hr. The reaction mixture was poured into water, and extracted with toluene. The combined organic phase was washed with water, dried over magnesium sulfate, and concentrated. The crude product was dissolved in a mixed solvent (220 ml) of THF/water (10:1) and triphenylphosphine (40 g) was added. The mixture was heated under reflux for 6 hr. After cooling to room temperature, the solvent was evaporated and 1N-hydrochloric acid (200 ml) was added to the residue. Unnecessary materials were removed by extraction with ethyl acetate. The aqueous phase was alkalified with potassium carbonate and extracted with chloroform. The extract was washed with water and saturated brine, dried over magnesium sulfate, and concentrated. Hydrochloric acid/ethanol was added to the obtained red oil to give (R)-acenaphthen-1-yl-amine hydrochloride (25 g) as yellow crystals.

$^1$H-NMR(DMSO-d$_6$)$\delta_{TMS}$: 3.32(d, J=17.3 Hz, 1H), 3.82 (dd, J=17.3, 8.1 Hz, 1H), 5.20(m, 1H), 7.40(d, J=6.8 Hz, 1H), 7.48(t, J=6.8 Hz, 1H), 7.55-7.62(m, 2H), 7.73(d, J=8.1 Hz, 1H), 7.85(d, J=7.8 Hz, 1H), 8.9(brs, 3H)

FAB-MS(M+H)$^+$: 170

(3) (R)-Acenaphthen-1-yl-amine.hydrochloride (25 g) was dissolved in water (200 ml) and the mixture was alkalified with potassium carbonate and extracted with chloroform. The extract was washed with water and saturated brine, dried over magnesium sulfate, and concentrated. The obtained (R)-acenaphthen-1-yl-amine (21 g, 124 mmol) was dissolved in ethanol (200 ml). Potassium carbonate (2.5 g, 18 mmol) and 1-ethyl-1-methyl-4-oxopiperidinium iodide (40 g) dissolved in water (100 ml) was added and the mixture was heated under reflux for 2 hr. The reaction mixture was poured into water, and the mixture was extracted with ethyl acetate. The extract was washed with water and saturated brine, dried over magnesium sulfate, and concentrated. The obtained residue was purified by silica gel column chromatography (chloroform/methanol) to give (R)-1-(acenaphthen-1-yl)-piperidin-4-one (22 g) as a red-yellow oil.

(4) A solution of (R)-1-(acenaphthen-1-yl)-piperidin-4-one (12.6 g, 50 mmol) and 1,2-phenylenediamine (10.8 g, 100 mmol) in THF (100 ml) was cooled to (0° C.), sodium triacetoxy borohydride (30 g) and acetic acid (12 ml) were added thereto, and the mixture was stirred at room temperature for 24 hr. The reaction mixture was poured into water, and potassium carbonate was added for neutralization. The mixture was extracted with ethyl acetate. The extract was washed with water and saturated brine, dried over sodium sulfate, and concentrated. The obtained residue was purified by silica gel column chromatography (chloroform/methanol) to give (R)-N-[1-(acenaphthen-1-yl)piperidin-4-yl]-benzene-1,2-diamine (9 g) as yellow crystals.

(5) (R)-N-[1-(Acenaphthen-1-yl)piperidin-4-yl]-benzene-1,2-diamine (9 g, 26 mmol) was dissolved in THF (100 ml), and carbonyldiimidazole (5 g, 30 mmol) was added. The mixture was stirred at room temperature for 2 hr. The reaction mixture was poured into water, and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give the title compound (8.8 g) as a white solid.

$^1$H-NMR(CDCl$_3$)$\delta_{TMS}$: 1.74-1.82(m, 2H), 2.36-2.60(m, 4H), 2.81(m, 1H), 3.01(m, 1H), 3.42(d, J=5.6 Hz, 2H), 4.29-4.36(m, 1H), 4.98(t, J=5.6 Hz, 1H), 7.01(m, 3H), 7.28-7.31 (m, 2H), 7.43-7.53(m, 3H), 7.60-7.62(m, 1H), 7.69(m, 1H), 9.56(brs, 1H)

FAB-MS(M+H)$^+$: 370

$[\alpha]_D^{20}$=52.5°

EXAMPLE 12

(S)-1-[1-(acenaphthen-1-yl)piperidin-4-yl]-1,3-dihydro-2H-benzoimidazol-2-one

The title compound was obtained as white crystals according to Example 11 and using (S)-2-methyl-CBS-oxazaborolidine (1 mol toluene solution).

$^1$H-NMR(CDCl$_3$)$\delta_{TMS}$: 1.74-1.82(m, 2H), 2.36-2.60(m, 4H), 2.81(m, 1H), 3.01(m, 1H), 3.42(d, J=5.6 Hz, 2H), 4.29-4.36(m, 1H), 4.98(t, J=5.6 Hz, 1H), 7.01(m, 3H), 7.28-7.31 (m, 2H), 7.43-7.53(m, 3H), 7.60-7.62(m, 1H), 7.69(m, 1H), 9.67(brs, 1H)

FAB-MS(M+H)$^+$: 370

$[\alpha]_D^{20}$=−52.6°

EXAMPLE 13

(R)-3-acetyl-1-[1-(acenaphthen-1-yl)piperidin-4-yl]-1,3-dihydro-2H-benzoimidazol-2-one (R)-1-[1-(Acenaphthen-1-yl)piperidin-4-yl]-1,3-dihydro-2H-benzoimidazol-2-one (6.2 g, 16.8 mmol) was dissolved in DMF (60 ml). Sodium hydride (0.9 g, 60%) was added and the suspension was stirred at 50° C. for 30 min. It was cooled to room temperature and acetyl chloride (1.5 g, 19 mmol) was added and the mixture was stirred for 3 hr. The reaction mixture was poured into water and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give the title compound (6.3 g) as pale-yellow crystals $^1$H-NMR(CDCl$_3$)$\delta_{TMS}$: 1.68-1.81(m, 2H), 2.40-2.56(m, 4H), 2.74(s, 3H), 2.78(m, 1H), 3.02(m, 1H), 3.42(m, 2H), 4.30(m, 1H), 4.98(m, 1H), 7.11-7.31(m, 4H), 7.45-7.71(m, 5H), 8.24(m, 1H)

FAB-MS(M+H)$^+$: 412

$[\alpha]_D^{20}$=40.1°

EXAMPLE 14

(R)-1-[1-(acenaphthen-1-yl)piperidin-4-yl]-3-methanesulfonyl-1,3-dihydro-2H-benzoimidazol-2-one The title compound was obtained as pale-yellow crystals according to Example 13 and using methanesulfonyl chloride.

$^1$H-NMR(CDCl$_3$)$\delta_{TMS}$: 1.71-1.85(m, 2H), 2.40-2.58(m, 4H), 2.85(s, 3H), 2.75(m, 1H), 3.02(m, 1H), 3.45(m, 2H), 4.28(m, 1H), 5.01(m, 1H), 7.1-7.31(m, 4H), 7.46-7.68(m, 5H), 8.28(m, 1H)

FAB-MS(M+H)$^+$: 448

$[\alpha]_D^{20}$=43.8°

EXAMPLE 15

Ethyl (R)-2-{3-[1-(acenaphthen-1-yl)piperidin-4-yl]-2,3-dihydro-2-oxo-benzoimidazol-1-yl}acetate (R)-1-[1-(Acenaphthen-1-yl)piperidin-4-yl]-1,3-dihydro-2H-benzoimidazol-2-one (2.3 g, 6 mmol) was dissolved in DMF (20 ml) and sodium hydride (300 mg, 60%) was added. The suspension was stirred at 50° C. for 30 min. After cooling to room temperature, ethyl bromoacetate (1.17 g, 7 mmol) was added and the mixture was stirred for 2 hr. The reaction mixture was poured into water, and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give the title compound (2.6 g) as pale-yellow crystals.

$^1$H-NMR(CDCl$_3$)$\delta_{TMS}$: 1.26(t, J=7.1, 3H), 1.82(m, 2H), 2.40-2.56(m, 4H), 2.78(m, 1H), 3.01((m, 1H), 3.44(m, 2H), 4.21(q, J=7.1 Hz, 2H), 4.35(m, 1H), 4.61(s, 2H), 4.99(m, 1H), 6.87(m, 1H), 7.07(m, 2H), 7.31(m, 2H), 7.45-7.55(m, 3H), 7.63(m, 1H), 7.71(m, 1H)

FAB-MS(M+H)$^+$: 456

$[\alpha]_D^{20}$=40.2°

EXAMPLE 16

(R)-2-{3-[1-(acenaphthen-1-yl)piperidin-4-yl]-2,3-dihydro-2-oxo-benzoimidazol-1-yl}acetic acid Ethyl (R)-2-{3-[1-(acenaphthen-1-yl)piperidin-4-yl]-2,3-dihydro-2-oxo-benzoimidazol-1-yl}acetate (2.6 g, 5.8 mmol) was dissolved in ethanol (10 ml), 2N-aqueous sodium hydroxide solution (10 ml) was added and the mixture was stirred at room temperature for 2 hr. The reaction mixture was poured into water, 1N-hydrochloric acid was added for neutralization, and the mixture was extracted with chloroform. The extract was washed with water and saturated brine, dried over magnesium sulfate, and concentrated. The obtained solid was washed with ethyl acetate to give the title compound (2.4 g) as pale-yellow crystals.

$^1$H-NMR(DMSO-d$_6$)$\delta_{TMS}$: 1.71-1.83(m, 2H), 2.63-3.10 (m, 5H), 3.30(m, 1H), 3.58-3.70(m, 2H), 4.49(m, 1H), 4.58(s, 2H), 5.36(m, 1H), 7.02-7.13(m, 2H), 7.14(d, J=6.8 Hz, 1H), 7.40(d, J=6.8 Hz, 1H), 7.52-7.65(m, 3H), 7.72(d, J=8.3 Hz, 1H), 7.84(d, J=8.3 Hz, 1H), 8.31(m, 1H), 12.08(brs, 1H)

FAB-MS (M+H)$^+$: 428

$[\alpha]_D^{20}$=42.5°

EXAMPLE 17

(R)-1-[1-(acenaphthen-1-yl)piperidin-4-yl]-3-(2-oxo-2-piperazin-1-ylethyl)-1,3-dihydro-2H-benzoimidazol-2-one dihydrochloride (1) (R)-2-{3-[1-(Acenaphthen-1-yl)piperidin-4-yl]-2,3-dihydro-2-oxo-benzoimidazol-1-yl}acetic acid (1.28 g, 3 mmol) was dissolved in DMF (15 ml). Boc-piperazine (0.56 g, 3 mmol), WSC.HCl (0.7 g, 3.6 mmol), HOBt (0.55 g, 2.4 mmol) and triethylamine (0.8 ml, 5.7 mmol) were added and the mixture was stirred at room temperature for 10 hr. The reaction mixture was poured into water, and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give a yellow solid (1.2 g).

(2) The above-mentioned compound was dissolved in 4N-hydrochloric acid/dioxane (10 ml) and the mixture was stirred at room temperature for 2 hr. The solvent was evaporated and isopropyl ether was added to the residue. The obtained crystals were collected by filtration to give the title compound (0.8 g) as yellow crystals.

$^1$H-NMR(DMSO-d$_6$)$\delta_{TMS}$: 1.76-1.88(m, 2H), 3.11-3.82 (m, 15H), 3.96(m, 1H), 4.71(m, 1H), 4.83(s, 2H), 5.63(m, 1H), 7.02-7.12(m, 3H), 7.46(d, J=6.8 Hz, 1H), 7.58(t, J=8.0 Hz, 1H), 7.67(t, J=7.8 Hz, 1H), 7.76-7.84(m, 2H), 7.92(m, 1H), 8.25(d, J=7.8 Hz, 1H), 9.58(brs, 2H), 12.28(brs, 1H)

FAB-MS(M+H)$^+$: 496

$[\alpha]_D^{20}$=48.5°

EXAMPLE 18

(R)-2-{3-[1-(acenaphthen-1-yl)piperidin-4-yl]-2,3-dihydro-2-oxo-benzoimidazol-1-yl}-N-methylacetamide (R)-2-{3-[1-(Acenaphthen-1-yl)piperidin-4-yl]-2,3-dihydro-2-oxo-benzoimidazol-1-yl}acetic acid (1 g, 2.3 mmol) was dissolved in DMF (10 ml). Methylamine hydrochloride (0.17 g, 2.5 mmol), WSC.HCl (0.53 g, 2.7 mmol), HOBt (0.43 g, 2.8 mmol) and triethylamine (0.7 ml, 5 mmol) were added and the mixture was stirred at room temperature for 15 hr. The reaction mixture was poured into water, and the mixture was extracted with ethyl acetate. The extract was washed with water and saturated aqueous ammonium chloride solution, dried over magnesium sulfate, and concentrated. The obtained residue was purified by silica gel column chromatography (chloroform/methanol) to give the title compound (0.7 g) as pale-yellow crystals.

$^1$H-NMR(DMSO-d$_6$)$\delta_{TMS}$: 1.59-1.70(m, 2H), 2.28-2.49 (m, 4H), 2.58(s, 3H), 2.95(m, 1H), 3.35-3.43(m, 3H), 4.16(m, 1H), 4.40(s, 2H), 4.96(m, 1H), 7.02(m, 3H), 7.28-7.33(m, 1H), 7.45-7.57(m, 3H), 7.65(d, J=8.3 Hz, 1H), 7.72(d, J=7.8 Hz, 1H), 8.08(m, 1H)

FAB-MS(M+H)$^+$: 441

$[\alpha]_D^{20}$=43.2°

EXAMPLE 19

(R)-2-{3-[1-(acenaphthen-1-yl)piperidin-4-yl]-2,3-dihydro-2-oxo-benzoimidazol-1-yl}-N,N-dimethylacetamide The title compound was obtained as pale-yellow crystals according to Example 18 and using dimethylamine hydrochloride.

1.76-$^1$H-NMR(CDCl$_3$)$\delta_{TMS}$: 1.84(m, 2H), 2.40-2.55(m, 4H), 2.78(m, 1H), 2.96(s, 3H), 3.01(m, 1H), 3.12(s, 3H), 3.45(m, 2H), 4.35(m, 1H), 4.66(s, 2H), 5.00(m, 1H), 6.99-7.07(m, 3H), 7.30(m, 2H), 7.45-7.70(m, 5H)

FAB-MS(M+H)$^+$: 455

$[\alpha]_D^{20}$=39.7°

EXAMPLE 20

(R)-2-{3-[1-(acenaphthen-1-yl)piperidin-4-yl]-2,3-dihydro-2-oxo-benzoimidazol-1-yl}acetamide (R)-2-{3-[1-(Acenaphthen-1-yl)piperidin-4-yl]-2,3-dihydro-2-oxo-benzoimidazol-1-yl}acetic acid (400 mg, 0.9 mmol) was dissolved in dichloromethane (10 ml). Thionyl chloride (0.2 ml, 2.7 mmol) was added under ice-cooling, and the mixture was stirred at room temperature for 2 hr. The solvent was evaporated and aqueous ammonia (5 ml) was added to the obtained residue under ice-cooling, and the mixture was further stirred under ice-cooling. The precipitated crystals were collected by filtration to give the title compound (0.22 g) as pale-yellow crystals.

$^1$H-NMR(DMSO-d$_6$)$\delta_{TMS}$: 1.62-1.70(m, 2H), 2.31-2.51 (m, 4H), 2.61(m, 1H), 2.97(m, 1H), 3.38(m, 2H), 4.18(m, 1H), 4.39(s, 2H), 4.97(m, 1H), 7.00-7.05(m, 3H), 7.22-7.33 (m, 3H), 7.45-7.73(m, 6H)

FAB-MS (M+H)$^+$: 427

$[\alpha]_D^{20}$=45°

FORMULATION EXAMPLE 1

Tablet

| | |
|---|---|
| compound of the present invention | 10.0 mg |
| lactose | 50.0 mg |
| corn starch | 20.0 mg |
| crystalline cellulose | 29.7 mg |
| polyvinylpyrrolidone K30 | 5.0 mg |
| talc | 5.0 mg |
| magnesium stearate | 0.3 mg |
| | 120.0 mg |

The compound of the present invention, lactose, corn starch and crystalline cellulose were mixed, kneaded with polyvinylpyrrolidone K30 paste solution, and granulated by passing a 20 mesh sieve. After drying at 50° C. for 2 hr, the granules were passed through a 24 mesh sieve, talc and magnesium stearate were admixed and tablets (120 mg per tablet) were produced using a pounder having a diameter of 7 mm.

FORMULATION EXAMPLE 2

Capsule

| | |
|---|---|
| compound of the present invention | 10.0 mg |
| lactose | 70.0 mg |
| corn starch | 35.0 mg |
| polyvinylpyrrolidone K30 | 2.0 mg |
| talc | 2.7 mg |
| magnesium stearate | 0.3 mg |
| | 120.0 mg |

The compound of the present invention, lactose, corn starch and crystalline cellulose were mixed, kneaded with polyvinylpyrrolidone K30 paste solution, and granulated by passing a 20 mesh sieve. After drying at 50° C. for 2 hr, the granules were passed through a 24 mesh sieve, admixed with talc and magnesium stearate and the mixture was filled in a hard capsule (No. 4) to give capsules (120 mg).

The test results in the following shows that the ORL-1 receptor agonist is useful for preventing and/or treating a sleep disorder, for example, a circadian rhythm sleep disorder such as jet-lag syndromes, a shift-work sleep disorder or delayed sleep phase syndromes.

Hereinbelow, pharmacological actions of the medicament of the present invention will be explained by Experimental Examples.

As the test compounds, the following 4 kinds of compounds were used.

compound A: (RS)-8-(acenaphthen-1-yl)-1-phenyl-1,3,8-triazaspiro[4.5]decan-4-one (synthesized according to the method described in Bioorganic & Medicinal Chemistry Letters, 1999, 9, 2343)

compound B: (R)-1-[1-(acenaphthen-1-yl)piperidin-4-yl]-1,3-dihydro-2H-benzoimidazol-2-one (compound of Example 11)

compound C: (R)-2-{3-[1-(acenaphthen-1-yl)piperidin-4-yl]-2,3-dihydro-2-oxo-benzoimidazol-1-yl}-N-methylacetamide (compound of Example 18)

compound D: N-(4-amino-2-methylquinolin-6-yl)-2-(4-ethylphenoxymethyl)benzamide hydrochloride (synthesized according to the method described in JTC-801, J. Med. Chem. 2000, 43, 4667)

EXPERIMENTAL EXAMPLE 1

ORL-1 Receptor Binding Test

Experimental Method and Measurement

Binding test of [$^3$H]-nociceptin was carried out using a standard product of the receptor prepared from cerebral cortex of rat. Specifically, 50 μl of a test substance solution of each concentration, 900 μl of a solution of the receptor standard product, and 50 μl of a labeled ligand [$^3$H]-nociceptin were added to a polypropylene tube successively, and were subjected to reaction at 25° C. for 20 minutes. The reaction solution was sucking-filtered with Whatman GF/B, glass filter in a cell harvester. The filter was three times washed with an ice-cooled, 50 mmol/l Tris/chloric acid buffer solution, and put into a measurement vial. ACS-II (2 ml, Amersham Pharmacia Biotech), liquid scintillation cocktail was added, and then the radioactivity was measured using a liquid scintillation counter (LSC-5100, ALOKA CO., LTD.). A non-labeled ligand test compound A was used to obtain the amount of non-specific binding. Binding inhibition (%) and inhibition constant (Ki value) were calculated according to the following calculation formulae.

Binding inhibition (%)={1−(B−N)/(T−N)}×100

N: Amount of non-specific binding, T: Amount of total binding, B: Amount of binding in the presence of test substance Inhibition constant (Ki value)=$IC_{50}$/(1+L/Kd)

Figure 1:
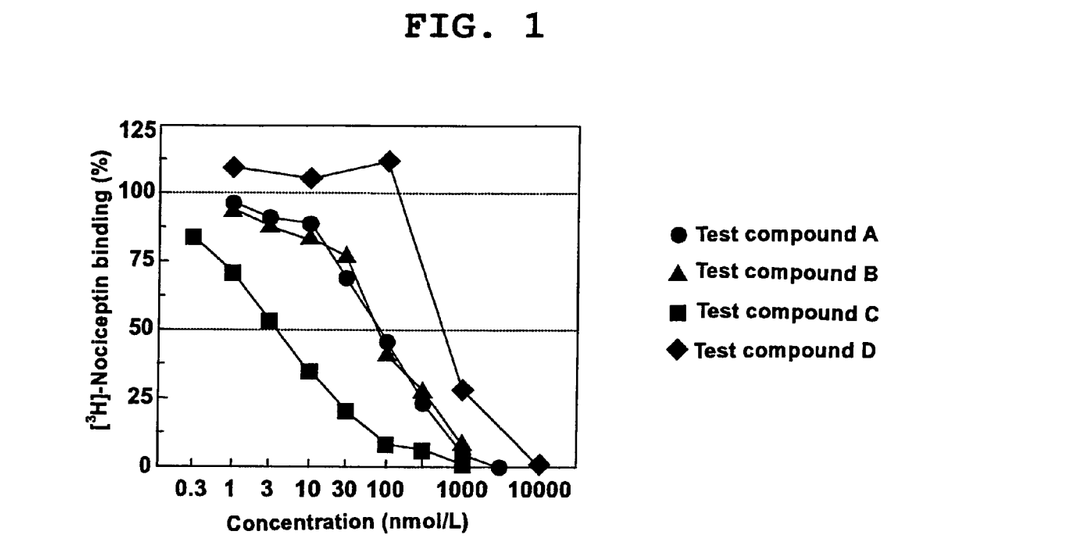
FIG. 1 shows the results of an ORL-1 receptor binding test.

$IC_{50}$: 50% Inhibition concentration, L: Concentration of a labeled ligand, Kd: Dissociation constant of a labeled ligand Results and Discussion As shown in FIG. 1, test compounds A, B, C and D inhibited the binding of [$^3$H]-nociceptin, depending on a concentration, and the $IC_{50}$ values were 84.2, 72.8, 4.4, 500 nmol/L, respectively. In addition, Ki values were 10.0, 8.4, 0.51 and 60.6 nmol/L, respectively.

From the above results, it was obvious that any one of test compounds A, B, C and D had affinity for an ORL-1 receptor.

EXPERIMENTAL EXAMPLE 2

Agonist Action

Experimental Method and Measurement

ORL-1 receptor agonistic activity was measured using HEK293 cells which strongly expressed a human ORL-1 receptor by the index of inhibiting activity for cAMP elevation by forskolin stimulation. In other words, cells expressing a human ORL-1 receptor was incubated overnight using a collagen-coated 96-well microplate, the incubation solution was discarded, and 100 μl of a Krebs-Ringer solution was added. Then, 50 μl of a test substance solution of each concentration was added, and was pre-incubated at 37° C. for 5 minutes. Further, 50 μl of a forskolin solution (1 μmol/L of a final concentration) was added and incubated at 37° C. for 15 minutes. After discarding the supernatant, 200 μl of a cell solubilizer was added to obtain a sample for cAMP assay in cells. cAMP concentration in the sample for cAMP assay was measured with BIOTRAK (Amersham Pharmacia Biotech), a kit for cAMP assay.

Results and Discussion

Figure 2:
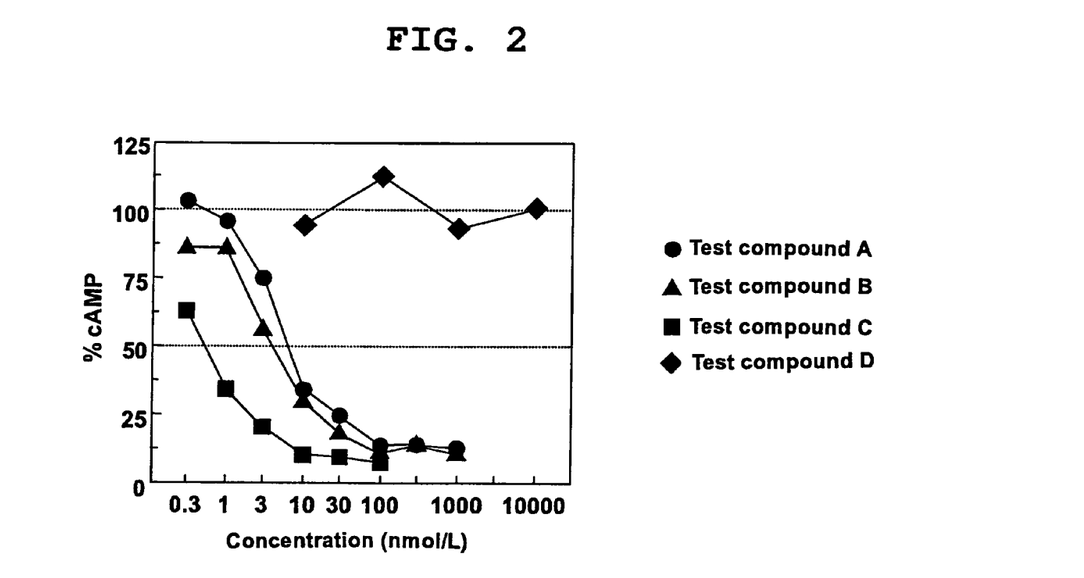
FIG. 2 shows the results of a cAMP assay.

As shown in FIG. 2, the test compounds A, B and C inhibited cAMP production depending on concentration. Therefore, it was obvious that the test compounds A, B and C had ORL-1 receptor agonistic activity. On the other hand, the test compound D did not inhibit cAMP production though it showed affinity for an ORL-1 receptor. In other words, it was obvious that the test compound D was ORL-1 receptor antagonist.

EXPERIMENTAL EXAMPLE 3

Phase Shift of Circadian Rhythm by the ORL-1 Receptor Agonist Under a Constant Dark Condition Experimental Method and Measurement The rats which had been previously subject to surgery to implant transmitter for measuring body temperature and activity (TA10TA-F20) in the peritoneal cavity, was used in this experiment. After a certain recovery period, the rats were put into a soundproof box having equipped with a signal-receiving board, and were raised individually under a constant dark condition. The body temperature and the activity of rats were measured automatically with a telemetry auto-measuring system every 5 minutes, and the results of the measurement were stored in a computer. The body-temperature rhythm was indicated by plotting time in horizontal axis, and days in vertical axis and temperatures higher than a mean body-temperature calculated by a least squares method were represented in a black line. After confirming that the body-temperature rhythm was recorded to be stable for 10 days or longer for a constant period, the ORL-1 receptor agonist was administered intraperitoneally every 3 hour at various times (CT0, CT3, CT6, CT9, CT12, CT15, CT18 and CT21 (CT: circadian time); the initiation time of body-temperature elevation under a constant dark condition was set to be CT12, and 1 day was represented as CT0 to CT24), to investigate for any phase shifts.

Results and Discussion

Figure 3:
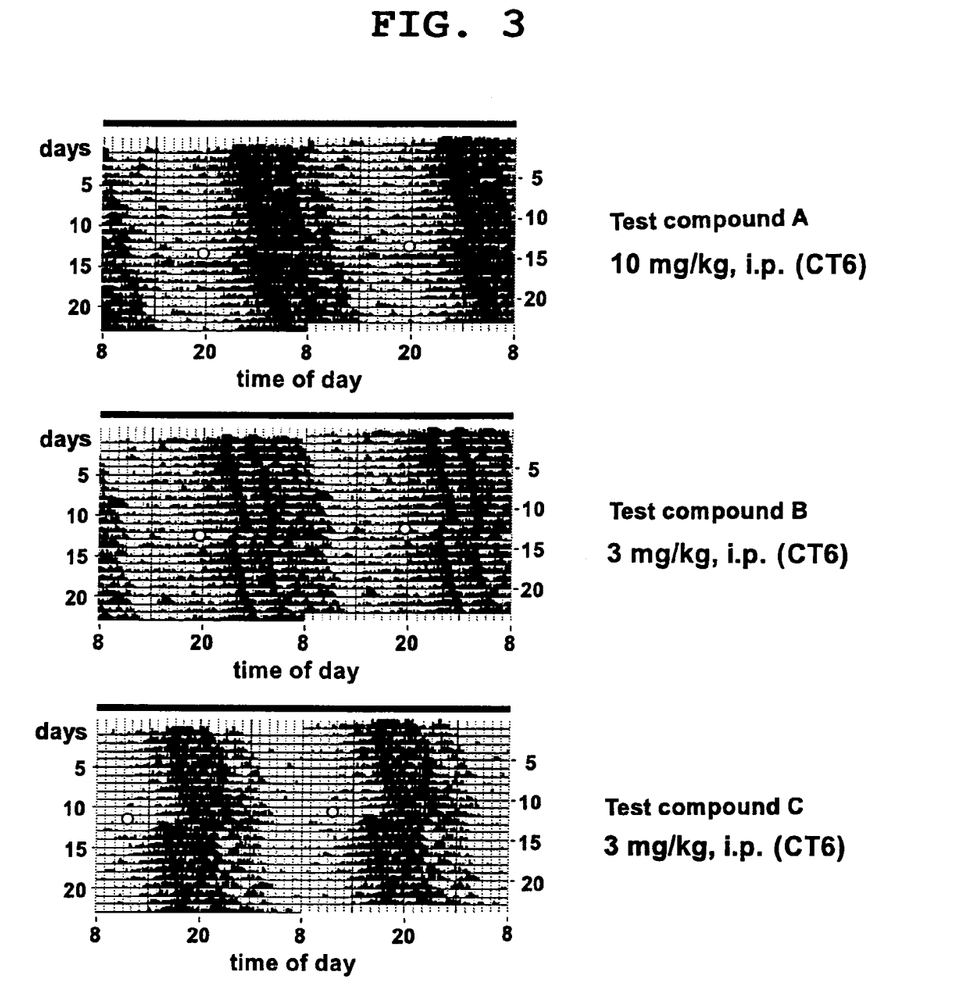
FIG. 3 shows a typical example of a phase shift of a circadian rhythm in rats by test compounds A, B and C, as ORL-1 receptor agonists.

FIG. 3 shows typical examples of a circadian rhythm phase shift when the test compounds A, B and C were administered at CT6. All of the test compounds A, B and C, which are ORL-1 receptors, showed a noticeable phase advancing action when administered at CT6 or CT9.

EXPERIMENTAL EXAMPLE 4

Antagonistic Action of the ORL-1 Receptor Antagonist on the Phase Advancement by the ORL-1 Receptor Agonist Experimental Method and Measurement The test compound D as an ORL-1 receptor antagonist was administered orally 1 hour before the test compound A or B was administered under the same constant dark condition as in Experimental Example 3, to investigate any phase shifts. The test compound A or B was administered intraperitoneally at CT6 when the most noticeable phase advancement was observed in Experimental Example 3.

Results and Discussion

Figure 4:
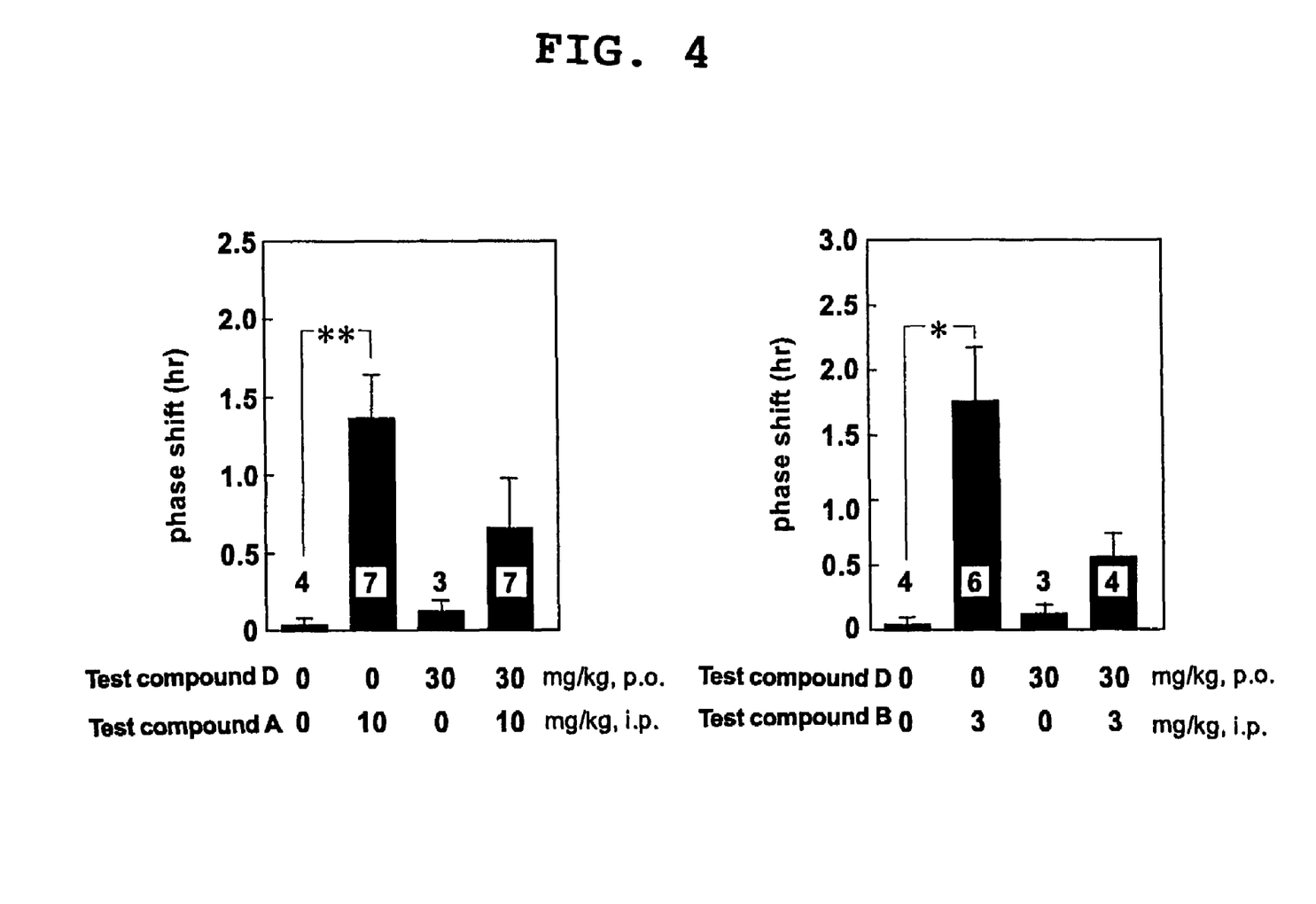
FIG. 4 shows actions of a test compound D, an ORL-1 receptor antagonist on phase advancing circadian rhythm in rats by test compounds A and B, as ORL-1 receptor agonists.

FIG. 4 shows the results of the action of the test compound D as an ORL-1 receptor antagonist, on the phase advancement by the test compounds A and B. The phase advancement by the ORL-1 receptor agonist, any of the test compounds A and B was antagonized by pre-administration of the test compound D, as an ORL-1 receptor antagonist. Therefore, the phase advancement by the test compounds A and B was considered as a reaction via the ORL-1 receptor. In addition, it was obvious that the ORL-1 receptor antagonist showed no phase shift from the fact that no phase shift was observed for the test compound D alone.

EXPERIMENTAL EXAMPLE 5

Action of the ORL-1 Receptor Agonist on Re-Entrainment of a Light-Dark Cycle

Experimental Method and Measurement

Rats were raised for 10 days or longer with a light-dark cycle of 12 hours (illumination in a light period; 150 lux). After confirming that body-temperature is recorded to be stably changed in a day, the light-dark cycle was advanced by 6 hours by advancing the initiation time of the light period by 6 hours. By a phase response curve obtained under a constant dark condition, the test substance C was administered at the administration time when the ORL-1 receptor agonist showed most phase advancing effect, namely, ZT6 (ZT: zeitgeber time, the initiation time of the light period was set to be ZT0, and 1 day was represented as ZT0 to ZT24), to investigate the influence on re-entrainment.

Results and Discussion

Figure 5:
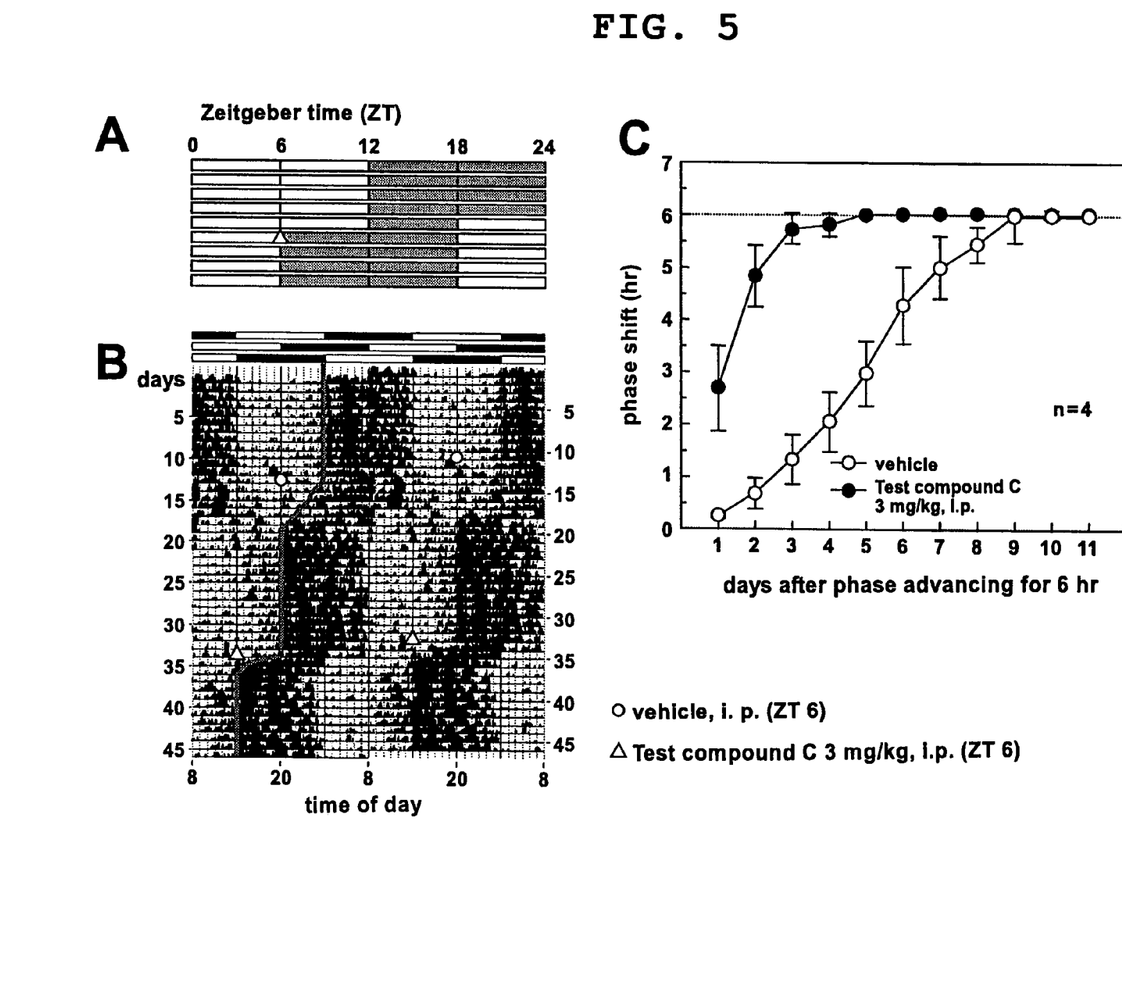
FIG. 5 shows actions of a test compound C as an ORL-1 receptor agonist on re-entrainment after a 6-hour advancement of a light-dark cycle. A: shift of the light-dark cycle and an administration timing, B: a typical example of a body-temperature rhythm re-entrainment, and C: summary of results of 4 examples.

FIG. 5 shows the results of the effect of test compound C on re-entrainment after a 6-hour advancement of the light-dark cycle. The time required for re-entrainment to a new light-dark cycle was 1 week or more for the vehicle-administered group. However, the test compound C-administered group was almost re-entrained to a new light-dark cycle in about 3 days after the advancement of the light-dark cycle. In other words, the ORL-1 receptor agonist showed effectiveness for an artificially prepared jet-lag model.

INDUSTRIAL APPLICABILITY

From the above-described pharmacological experiments, a medicament containing the ORL-1 receptor agonist, is useful for preventing and/or treating a sleep disorder, for example, a circadian rhythm sleep disorder such as jet-lag syndromes, a shift-work sleep disorder or delayed sleep phase syndromes.

This application is based on a patent application No. 2002-93398 filed in Japan, the contents of which are hereby incorporated by reference.

The invention claimed is:

1. A compound represented by the formula (I)

(I)

wherein $R^1$ is lower alkyl-C(O)$NR^3R^4$, $R^2$ is hydrogen, lower alkyl, halogen, lower alkoxy, phenoxy, benzyloxy, trifluoromethyl, nitro, amino or cyano, and $R^3$ and $R^4$ may be the same or different, and each is hydrogen, lower alkyl or lower alkenyl, or $R^3$ and $R^4$ may bind with an adjacent nitrogen atom to form a saturated nitrogen-containing hetero ring (the hetero ring may be substituted with lower alkyl, halogen, lower alkoxy, phenoxy or benzyloxy), a racemic mixture thereof, an enantiomer corresponding thereto or a pharmaceutically acceptable salt thereof.

2. The compound of claim 1, wherein $R^2$ is hydrogen, a racemic mixture thereof, an enantiomer corresponding thereto or a pharmaceutically acceptable salt thereof.

3. The compound of claim 1, wherein $R^1$ is lower alkyl-C(O)$NR^3R^4$ (either $R^3$ or $R^4$ is hydrogen) or lower alkyl-C(O)$NR^3R^4$ wherein $R^3$ and $R^4$ bind with an adjacent nitrogen atom to form a saturated nitrogen-containing hetero ring (the hetero ring may be substituted with lower alkyl, halogen, lower alkoxy, phenoxy or benzyloxy), a racemic mixture thereof, an enantiomer corresponding thereto or a pharmaceutically acceptable salt thereof.

4. The compound of claim 1, which is (R)-2-{3-[1-(acenaphthen-1-yl)piperidin-4-yl]-2,3-dihydro-2-oxo-benzoimidazol-1-yl}-N-methylacetamide, a racemic mixture thereof, an enantiomer corresponding thereto or a pharmaceutically acceptable salt thereof.

5. A pharmaceutical composition comprising an effective amount of the compound of claim 1, a racemic mixture thereof, an enantiomer corresponding thereto or a pharmaceutically acceptable salt thereof and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,566,728 B2 | Page 1 of 1 |
| APPLICATION NO. | : 10/508339 | |
| DATED | : July 28, 2009 | |
| INVENTOR(S) | : Teshima et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1145 days.

Signed and Sealed this
Twenty-second Day of March, 2011

David J. Kappos
*Director of the United States Patent and Trademark Office*